United States Patent [19]

Sejpka et al.

[11] Patent Number: 5,831,080
[45] Date of Patent: Nov. 3, 1998

[54] PROCESS FOR PREPARING ORGANOSILICON COMPOUNDS CONTAINING GLYCOSIDE RADICALS

[75] Inventors: Johann Sejpka, Marktl; Franz Wimmer, Burghausen, both of Germany

[73] Assignee: Wacker-Chemie GmbH, Germany

[21] Appl. No.: 635,809

[22] Filed: Apr. 22, 1996

Related U.S. Application Data

[63] Continuation of Ser. No. 188,867, Jan. 31, 1994, abandoned.

[30] Foreign Application Priority Data

Feb. 26, 1993 [DE] Germany .......................... 43 06 041.2

[51] Int. Cl.$^6$ ............................... C08B 37/00; C07F 7/18
[52] U.S. Cl. ........................ 536/124; 536/4.1; 536/17.1; 536/120; 536/121; 556/465; 556/466; 556/482
[58] Field of Search .................... 536/4.1, 17.1, 536/120, 121, 124; 556/465, 466, 482

[56] References Cited

U.S. PATENT DOCUMENTS

| | | | |
|---|---|---|---|
| 3,219,656 | 11/1965 | Boettner et al. | 536/18.3 |
| 3,707,535 | 12/1972 | Lew | 536/18.6 |
| 3,839,318 | 10/1974 | Mansfield | 536/18.6 |
| 4,950,743 | 8/1990 | McCurry, Jr. et al. | 536/18.6 |
| 4,992,538 | 2/1991 | Sau | 536/84 |
| 5,047,492 | 9/1991 | Weidner et al. | 528/15 |
| 5,071,978 | 12/1991 | Sau | 536/124 |
| 5,133,897 | 7/1992 | Balzer | 252/312 |
| 5,171,476 | 12/1992 | Bloodworth et al. | 252/314 |

FOREIGN PATENT DOCUMENTS

| | | |
|---|---|---|
| 393509B | 11/1991 | Austria . |
| 0348705 | 1/1990 | European Pat. Off. . |
| 0416402 | 3/1991 | European Pat. Off. . |
| 0452067 | 10/1991 | European Pat. Off. . |
| 0519683 | 12/1992 | European Pat. Off. . |
| 3837397 | 5/1990 | Germany . |
| 3925846 | 2/1991 | Germany . |

OTHER PUBLICATIONS

Agaskar et al. *J. Am. Chem. Soc.* vol. 109, No. 18, 1987, A new route to trimethylsilylated spherosilicates, pp. 5554–5556.

I. Hasegawa, S. Sakka, ACS Symp. Ser. 398 (1989) 140, Silicate Species with Cagelike Structure in Solutions and Rapid Solidification with Organic Quaternary Ammonium Ions.
I. Hasegawa, S. Sakka, J. Mol. Liqu. 34 (1987) 307–315, the Effect of Tetramethylammonium ions on the distribution of Silicate species in the Methanolic Solutions.
D. Hoebbel, W. Wieker, H. Jancke, G. Engelhard, Z. Chem. 14(3), (1974) 109 Strukturuntersuchungen an Silikatanionen in wäβriger Lösung mit Hilfe der $^{29}$Si–NMR–Spektroskopi.
D. Hoebbel, W. Wieker, Z. Allg. Anorg. Chem., 384 (1971) 43–52 Die Konstitution des Tetramethylammoniumsilicats der Zusammensetzung 1, ON(CH3)4 . . . .
C.A. of EP 348 705, Jan. 3, 1990, Chemical Abstracts answer No. 90–008778/02.
Elbin et al. *Clin. Chem.* Jan. 1993, 39(1), 112–118.

*Primary Examiner*—Kathleen K. Fonda
*Attorney, Agent, or Firm*—Brooks & Kushman P.C.

[57] ABSTRACT

The present invention relates to organosilicon compounds containing glycoside radicals, having units of the formula $$R_aR^1_bSiO_{\frac{4-a-b}{2}} \qquad (I)$$

in which
R is identical or different and represents a hydrogen atom or an organic radical,
a is 0, 1, 2 or 3,
b is 0, 1, 2 or 3 and
$R^1$ can be identical or different and represents a radical of the formula $$Z-(R^2O)_c-R^3- \qquad (II)$$

in which
Z represents a glycoside radical which is built up from 1 to 10 monosaccharide units,
$R^2$ can be identical or different and represents an alkylene radical,
c is 0 or a number from 1 to 20, and
$R^3$ represents an alkylene radical, with the proviso that the sum of a and b is less than or equal to 3 and the organosilicon compound comprising units of the formula (I) contains at least one radical $R^1$ per molecule.

1 Claim, No Drawings

PROCESS FOR PREPARING ORGANOSILICON COMPOUNDS CONTAINING GLYCOSIDE RADICALS

The application is a continuation of application Ser. No. 08/188,867, filed on Jan. 31, 1994, now abandoned.

FIELD OF INVENTION

The present invention relates to organosilicon compounds containing glycoside radicals, processes for their preparation and their use.

BACKGROUND OF INVENTION

Alkyl (poly)glycosides and alkylpolyalkoxyalkyl glucosides and their use as surfactants, emulsifiers and foam stabilizers are already known. In this context, reference may be made to, for example, U.S. Pat. No. 3,219,656 (Rohm & Haas Co.; issued Nov. 23, 1965), U.S. Pat. No. 4,950,743 (Henkel KGaA; published Aug. 21, 1990) and DE 39 25 846 (Hüls AG; published Feb. 14, 1991) and the corresponding U.S. Pat. No. 5,133,897 (issued Jul. 28, 1992).

SUMMARY OF INVENTION

The present invention relates to organosilicon compounds containing glycoside radicals, containing units of the formula $$R_a R^1_b SiO_{\frac{4-a-b}{2}} \qquad (I)$$

in which
R can be identical or different and represents a hydrogen atom or an organic radical,
a is 0, 1, 2 or 3,
$R^1$ can be identical or different and represents a radical of the formula $$Z—(R^2 O)_c—R^3— \qquad (II)$$

b is 0, 1, 2 or 3 and
in which
Z represents a glycoside radical having from 1 to 10, preferably 1 to 4 and more preferably 1 or 2, monosaccharide units,
$R^2$ can be identical or different and represents an alkylene radical,
c is 0 or a number from 1 to 20, preferably 0 or a number from 1 to 15, more preferably 0 or a number from 1 to 4, and
$R^3$ represents an alkylene radical,
with the proviso that the sum of a and b is less than or equal to 3 and the organosilicon compound comprising units of the formula (I) contains at least one radical $R^1$ per molecule.

The radical R is preferably an optionally substituted hydrocarbon radicals having 1 to 18 carbon atoms, alkyl radicals having 1 to 4 carbon atoms, the methyl radical being particularly preferred.

Examples of radical R are alkyl radical, such as the methyl, ethyl, n-propyl, iso-propyl, n-butyl, iso-butyl, tert-butyl, n-pentyl, iso-pentyl, neo-pentyl and tert-pentyl radical, hexyl radicals, such as the n-hexyl radical, heptyl radicals, such as the n-heptyl radical, octyl radicals, such as the n-octyl radical and iso-octyl radicals, such as the 2,2,4-trimethylpentyl radical, nonyl radicals, such as the n-nonyl radical, decyl radicals, such as the n-decyl radical, dodecyl radicals, such as the n-dodecyl radical, and octadecyl radicals, such as the n-octadecyl radical; alkenyl radicals, such as the vinyl, allyl, n-5-hexenyl, 4-vinylcyclohexyl and the 3-norbornenyl radical; cycloalkyl radicals, such as cyclopentyl, cyclohexyl, 4-ethylcyclohexyl and cycloheptyl radicals, norbornyl radicals and methylcyclohexyl radicals; aryl radicals, such as the phenyl, biphenylyl, naphthyl and anthryl and phenanthryl radical; alkaryl radicals, such as o-, m- and p-tolyl radicals, xylyl radicals and ethylphenyl radicals; and aralkyl radicals, such as the benzyl radical and the α,β-phenylethyl radical.

Examples of monosaccharides from which the glycoside radicals Z can be built up are hexoses and pentoses, such as glucose, fructose, galactose, mannose, talose, allose, altrose, idose, arabinose, xylose, lyxose and ribose, glucose being preferred.

Examples of alkylene radicals are methylene, ethylene, propylene, butylene, pentylene, hexylene, heptylene, octylene, nonylene, decylene and octadecylene radicals.

The radicals $R^2$ is preferably the ethylene radical and the 1,2-propylene radical, the ethylene radical being more preferred.

The radical $R^3$ is preferably linear alkylene radicals having from 2 to 20 carbon atoms, more preferably linear alkylene radicals having from 2 to 8 carbon atoms, in particular the n-propylene radical.

Examples of radicals $R^1$ are G—$CH_2CH_2CH_2$—, G—$(CH_2CH_2O)$—$CH_2CH_2CH_2$—, G—$(CH_2CH_2O)_2$—$CH_2CH_2CH_2$—,

G—$(CH_2CHO)$—$CH_2CH_2CH_2$—,

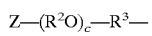
G—$(CH_2CHO)_2$—$CH_2CH_2CH_2$—, $$\overset{CH_3}{\underset{|}{G—(CH_2CH_2O)—CH_2CH_2CHCH_2—,}}$$

$$\overset{CH_3}{\underset{|}{G—(CH_2CH_2O)_2—CH_2CH_2CHCH_2—,}}$$

in which G represents a glucoside radical ($C_6H_{11}O_6$—), $G_2$—$CH_2CH_2CH_2$—, $G_2$—$(CH_2CH_2O)$—$CH_2CH_2CH_2$—, $G_2$—$(CH_2CH_2O)_2$—$CH_2CH_2CH_2$—, $$\overset{CH_3}{\underset{|}{G_2—(CH_2CHO)—CH_2CH_2CH_2—,}}$$

$$\overset{CH_3}{\underset{|}{G_2—(CH_2CHO)_2—CH_2CH_2CH_2—,}}$$

$$\overset{CH_3}{\underset{|}{G_2—(CH_2CH_2O)—CH_2CH_2CHCH_2—}} \quad \text{and}$$

$$\overset{CH_3}{\underset{|}{G_2—(CH_2CH_2O)_2—CH_2CH_2CHCH_2—}}$$

in which $G_2$ represents a glycoside radical built up from two glucose units.

The radical $R^1$ is preferably G—$CH_2CH_2CH_2$—, G—$(CH_2CH_2O)$—$CH_2CH_2CH_2$—, $G_2$—$CH_2CH_2CH_2$— and $G_2$—$(CH_{2CH2}O)$—$CH_2CH_2CH_2$—, G—$(CH_2CH_2O)$—$CH_2CH_2CH_2$— and $G_2$—$(CH_2CH_2O)$—$CH_2CH_2CH_2$— being preferred and G represents a glucoside radical ($C_6H_{11}O_6$—) and $G_2$ represents a glycoside radical built up from two glucose units.

The organosilicon compounds according to the invention containing glycoside radicals are preferably those of the formula

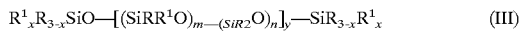  (III)

in which R and R$^1$ have the above meaning, m can be identical or different and is 0 or a number of from 1 to 200, preferably 0 or a number of from 1 to 100, and more preferably 0 or a number of from 1 to 50, n can be identical or different and is 0 or a number of from 1 to 1000, preferably 0 or a number of from 1 to 500, and more preferably 0 or a number of from 1 to 100, x is 0 or 1 and y is 0 or a number of from 1 to 1200, preferably 0 or a number of from 1 to 600, more preferably 0 or a number of from 1 to 100, with the proviso that the compound of the formula (III) contains at least one radical R$^1$.

If m in the organosilicon compounds according to formula (III) containing glycoside radicals is on an average other than 0, x is preferably 0.

If x in the organosilicon compounds according to formula (III) containing glycoside radicals is on an average other than 0, m is preferably 0.

Although not shown by formula (III), up to 10 mol percent of the diorganosiloxane units can be replaced by other siloxane units, such as, RSiO$_{3/2}$, R$^1$SiO$_{3/2}$ and/or SiO$_{4/2}$ units, in which R and R$^1$ have the meaning given above.

The organosilicon compounds according to the invention containing glycoside radicals can be prepared by various processes.

PROCESS 1

The present invention relates to a process for the preparation of the organosilicon compounds containing glycoside radicals, which comprises, in a first stage reacting a mono- and/or oligosaccharide (1) with a compound (2) of the formula HO—(R$^2$O)$_c$—R$^4$  (IV)

in which

R$^2$ can be identical or different and represents an alkylene radical, c is 0 or a number from 1 to 20, preferably 0 or a number from 1 to 15, more preferably 0 or a number from 1 to 4, and R$^4$ represents an alkenyl radical, and in a second stage reacting the glycoside obtained in the first stage with an organo-silicon compound (3) containing Si-bonded hydrogen, containing units of the formula

  (V)

in which

R$^5$ can be identical or different and represents an organic radical, d is 0, 1, 2 or 3 and e is 0, 1, 2 or 3, with the proviso that the sum of d+e is less than or equal to 3 and the organosilicon compound comprising units of the formula (V) contains at least one Si-bonded hydrogen atom per molecule.

Examples of the saccharides (1) are the examples mentioned above for monosaccharides, sucrose, lactose, maltose, raffinose and hydrates thereof, glucose or glucose monohydrate being preferably employed in the first stage of process 1 according to the invention.

The radical R$^4$ is preferably ω-alkenyl groups, such as the vinyl, allyl, 3-butenyl and the 3-methyl-3-butenyl radical, the allyl radical being more preferred.

Examples of compounds (2) are HO—CH$_2$CH=CH$_2$,

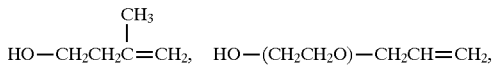

HO—(CH$_2$CH$_2$O)$_2$—CH$_2$CH=CH$_2$,

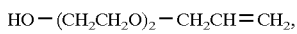

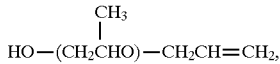

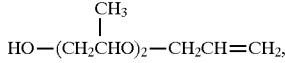

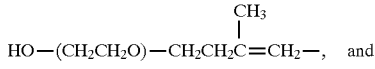 and

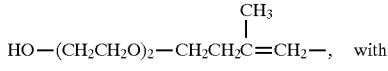 with

HO—CH$_2$CH=CH$_2$,

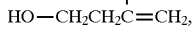

HO—(CH$_2$CH$_2$O)—CH$_2$CH=CH$_2$, and HO—(CH$_2$CH$_2$O)$_2$—CH$_2$CH=CH$_2$ being preferred and HO—CH$_2$CH=CH$_2$ and HO—(CH$_2$CH$_2$O)—CH$_2$CH=CH$_2$ being more preferred.

The organosilicon compounds (3) employed in the second stage of process 1 according to the invention are preferably α-hydridoorganopolysiloxanes and α,ω-dihydridoorganopolysiloxanes, such as H—Si(CH$_3$)$_2$—O—Si(CH$_3$)$_3$, H—Si(CH$_3$)$_2$—O—Si(CH$_3$)$_2$—H, H—[Si(CH$_3$)$_2$—O]$_4$—Si(CH$_3$)$_2$—H, H—[Si(CH$_3$)$_2$—O]$_9$—Si(CH$_3$)$_2$—H, H—Si(CH$_3$)$_2$—O—[Si(CH$_3$)$_2$—O]$_{15}$—Si(CH$_3$)$_2$—H, H—Si(CH$_3$)$_2$—O—[Si(CH$_3$)$_2$—O]$_{18}$—Si(CH$_3$)$_2$—H, H—Si(CH$_3$)$_2$—O—[Si(C$_2$H$_5$)$_2$—O]$_{10}$—Si(CH$_3$)$_2$—H, organopolysiloxanes containing α,ω-triorganylsiloxy groups and Si-bonded hydrogen, such as, (CH$_3$)$_3$SiO—SiHCH$_3$O—Si(CH$_3$)$_3$, (CH$_3$)$_3$SiO[SiHCH$_3$O]$_2$Si(CH$_3$)$_3$, (CH$_3$)$_3$SiO[SiHCH$_3$O]$_3$Si(CH$_3$)$_3$, (CH$_3$)$_3$SiO[SiHCH$_3$O]$_4$Si(CH$_3$)$_3$ and (CH$_3$)$_3$SiO[Si(CH$_3$)$_2$O]$_{50}$[SiHCH$_3$O]$_5$Si(CH$_3$)$_3$, H—Si(CH$_3$)$_2$—O—Si(CH$_3$)$_3$, and (CH$_3$)$_3$SiO—SiHCH$_3$O—Si(CH$_3$)$_3$ being more preferred.

Examples of radical R$^5$ are the examples given above for R.

In the first stage of process 1, according to the invention, the molar ratio of saccharide (1) employed to compound (2) is preferably 1:1 to 1:4, more preferably 1:2 to 1:3.

The first stage of process 1 according to the invention is preferably carried out in the presence of an organic or inorganic acid.

Examples of such acids are inorganic acids, such as HCl, HClO$_4$, H$_2$SO$_4$ and H$_3$PO$_4$, and organic acids, such as acetic acid, formic acid, propionic acid, p-toluenesulfonic acid, methanesulfonic acid, trifluoromethanesulfonic acid and dodecylbenzenesulfonic acid, p-toluenesulfonic acid and trifluoromethanesulfonic acid being more preferably employed.

The acid is preferably employed in process 1 according to the invention in amounts of 0.05 to 5.0% by weight, more preferably 0.5 to 2.0% by weight, based on the total weight of saccharide (1).

If desired, the acid can be added in a mixture with water and/or an organic solvent.

The first stage of process 1 according to the invention is carried out at a temperature of preferably 85° to 120° C., preferably 95° to 110° C., under a pressure of preferably 20 to 150 hPa, more preferably 50 to 120 hPa.

When the reaction of the first stage has ended, the acid is advantageously neutralized and excess compound (2) is removed in a known manner, for example by distillation, it being possible, if desired, to add an organic solvent which has a higher boiling point than the compound (2) to the reaction mixture before distillation of excess compound (2).

Examples of bases which can be employed for neutralization of the acid in the first stage of process 1 according to the invention are alkali metal hydroxides, such as sodium hydroxide and potassium hydroxide, alkali metal siliconates, amines, such as, methylamine, dimethylamine, ethylamine, diethylamine, triethylamine and n-butylamine and ammonium compounds, such as, tetramethylammonium hydroxide, sodium hydroxide being more preferred.

If desired, the base can be added as a mixture with water and/or an organic solvent.

The alkenyl glycosides obtained in the first stage of process 1 according to the invention are then reacted in a second stage with organosilicon compounds (3) in the manner known for addition of Si-bonded hydrogen on the aliphatic carbon-carbon multiple bond.

In the second stage of process 1, according to the invention, the molar ratio of alkenyl glycoside to organosilicon compound (3) is preferably 1:1 to 1:2, more preferably 1:1 to 1:1.5.

The reaction of the second stage is preferably carried out in the presence of a catalyst which promotes addition of Si-bonded hydrogen onto an aliphatic multiple bond.

The same catalysts which were possible to employ to date for promoting addition of Si-bonded hydrogen onto an aliphatic double bond can be employed as catalysts which promote addition of Si-bonded hydrogen onto an aliphatic double bond. The catalysts are preferably a metal from the platinum metals group or a compound or a complex from the platinum metals group.

Examples of such catalysts are metallic and finely divided platinum, which can be on supports, such as silicon dioxide, aluminum oxide or active charcoal, or compounds or complexes of platinum, such as platinum halides, for example $PtCl_4$, $H_2PtCl_6.6H_2O$ or $Na_2PtCl_4.4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6.6H_2O$ and cyclohexanone, platinum-vinylsiloxane complexes, such as platinum-1,3-divinyl-1,1,3,3-tetramethyldisiloxane complexes with or without a content of detectable inorganically bonded halogen, bis(γ-picoline)platinum dichloride, trimethylene-dipyridineplatinum dichloride, dicyclopentadieneplatinum dichloride, dimethylsulfoxide-ethyleneplatinum(II) dichloride, cyclooctadiene-platinum dichloride, norbornadiene-platinum dichloride, γ-picoline-platinum dichloride, cyclopentadiene-platinum dichloride and reaction products of platinum tetrachloride with olefin and primary amine or secondary amine or primary and secondary amine, such as the reaction product of platinum tetrachloride dissolved in 1-octene with sec-butylamine, $PtCl_4$, $H_2PtCl_6.6H_2O$ and platinum-olefin complexes preferably being employed and $H_2PtCl_6.6H_2O$ more preferably being employed.

The catalyst is preferably employed in amounts of 0.1 to 1000 ppm by weight, preferably in amounts of from 1 to 50 ppm by weight, calculated as elemental platinum and based on the total weight of alkenyl glycoside and organosilicon compound (3).

The reaction of the second stage of process 1 according to the invention is preferably carried out under a pressure of between 900 and 1100 hPa and at a temperature of preferably 50° to 150° C., more preferably 80° to 140° C.

The second stage of process 1 according to the invention can be carried out in the presence or absence of organic solvents. If solvents are used, those in which the alkenyl glycoside prepared in the first stage dissolves at least partly, preferably completely are preferred.

Examples of solvents which may be employed are toluene, xylene and isopropanol, toluene and isopropanol being particularly preferred.

Preferably, no solvent is employed in process 1 according to the invention.

According to a preferred embodiment of process 1 according to the invention,
in a first stage
a mixture of glucose monohydrate and compound (2), in particular $HOCH_2CH_2OCH_2CH=CH_2$, is heated to about 100° C. under reduced pressure, acid, in particular p-toluenesulfonic acid, is added and the components are allowed to react, volatile constituents being removed by distillation, and
in a second stage
the alkenyl glycoside obtained in the first stage is reacted with an organosilicon compound (3) in the presence of a catalyst.

Process 1 according to the invention has the advantage that it is easy to carry out and very high yields are achieved. Further, Process 1 has the advantage that volatile constituents and any optional solvents employed can be recovered by distillative working up and can be re-used.

PROCESS 2

Another possibility for preparation of the organosilicon compounds according to the invention containing glycoside radicals comprises first reacting a compound (2) with an organosilicon compound (3) and then reacting the resulting organosilicon compound containing hydroxyalkyl functional groups with a saccharide (1).

The present invention further relates to a process for the preparation of the organosilicon compounds according to the invention containing glycoside radicals, which comprises,
in a first stage
reacting compound (2) with an organosilicon compound (3), and then
in a second stage
reacting the organosilicon compound obtained in the first stage with a saccharide (1).

Examples of and preferred and particularly preferred species of the saccharide (1), the compound (2) and the organosilicon compound (3) are the examples and preferred and more preferably species mentioned for process 1.

The first stage of process 2 according to the invention is preferably carried out in the presence of a catalyst which promotes addition of Si-bonded hydrogen onto an aliphatic carbon-carbon multiple bond. Examples of and particularly preferred species of catalyst are the examples mentioned for process 1.

The catalyst is preferably employed in amounts of 0.1 to 1000 ppm by weight, preferably in amounts of 1 to 50 ppm by weight, calculated as elemental platinum and based on the total weight of the compound (2) and organosilicon compound (3).

In the first stage of process 2 according to the invention, the molar ratio of compound (2) to organosilicon compound (3) is preferably 1:1 to 1:2, more preferably 1:1 to 1:1.5.

The reaction in the first stage of process 2 according to the invention is preferably carried out under a pressure of between 900 and 1100 hPa and at a temperature of preferably 50° to 150° C., more preferably 80° to 140° C.

The first stage of process 2 according to the invention can be carried out in the presence or absence of organic solvents, it being possible for the solvents to be the organic solvents mentioned above for process 1. Preferably, no solvent is employed in the first stage of process 2.

When the reaction in the first stage has ended, excess compound (2) is advantageously removed in a known manner, for example by distillation, it being possible for an organic solvent which has a higher boiling point than the compound(2) to be added to the reaction mixture before distillation of excess compound (2).

The organosilicon compounds obtained in the first stage of process 2 according to the invention are then reacted with saccharide (1) in a second stage.

In the second stage of process 2 according to the invention, the molar ratio of saccharide (1) employed to organosilicon compound prepared in the first stage is preferably 1:1 to 1:3, more preferable 1:1 to 1:2. The second stage of process 2 according to the invention is preferably carried out in the presence of an organic or inorganic acid.

Examples of and particularly preferred species of the acid employed are the examples and particularly preferred species mentioned for process 1.

The acid is preferably employed in process 2 according to the invention in amounts of 0.05 to 5.0% by weight, particularly preferably 0.5 to 2.0% by weight, based on the total weight of saccharide (1).

The second stage of process 2 according to the invention is carried out at a temperature of preferably 85° to 120° C., more preferably 95° to 110° C., under a pressure of preferably 20 to 200 hPa, more preferably 50 to 150 hPa.

When the reaction of the second stage has ended, the acid is advantageously neutralized and the organosilicon compound according to the invention is isolated.

All the bases described in process 1 can be employed for neutralization of the acid.

The components employed in process 1 and in process 2 can be one type of such a component or a mixture of at least two types of such components.

The organosilicon compounds containing glycoside radicals prepared by processes 1 and 2 according to the invention are in each case mixtures of various isomeric forms, and can exist side by side with α- and β-glycosidic bonds.

The organosilicon compounds according to the invention containing glycoside radicals have the advantage that they are highly compatible with other organosilicon compounds and are therefore suitable, for example, for use in compositions comprising organopolysiloxane. Furthermore, the organosilicon compounds according to the invention have the advantage of being largely biologically degradable. Moreover, the organosilicon compounds according to the invention containing glycoside radicals have the advantage that they have a foam-stabilizing and also foam-forming action and can be employed as wetting agents.

The organosilicon compounds according to the invention containing glycoside radicals can be employed for all purposes for which alkyl (poly)glycosides have been used to date. The organosilicon compounds according to the invention containing glycoside radicals can thus be employed, in particular, as surfactants. It is found to be advantageous here that they are highly compatible with other surfactants. Because of the mild surfactant action of the substances according to the invention, they are excellently suitable for cosmetic and pharmaceutical applications. Since the organosilicon compounds according to the invention containing glycoside radicals themselves, and aqueous solutions thereof, foam to a high degree, they are particularly suitable as additives for cleaning agents. The organosilicon compounds according to the invention can be further employed as emulsifiers for synthetic and naturally occurring oils as well as waxes.

In the examples described below, all the parts and percentages data relate to the weight, unless stated otherwise. Furthermore, all the viscosity data relate to a temperature of 25° C. Unless stated otherwise, the following examples were carried out under a pressure of the surrounding atmosphere, about 1000 hPa, and at room temperature, about 20° C., or a temperature which is established when the reactants are brought together at room temperature without additional heating or cooling.

EXAMPLE 1

(A) Preparation of alkenyl glycoside I 153 g of HO—CH$_2$CH$_2$O—CH$_2$CH=CH$_2$ (referred to as "allyl glycol" hereafter) are mixed with 99 g of glucose monohydrate and the mixture is first stirred under a pressure of 60 hPa and at a temperature of 65° C. for a period of one hour and then under a pressure of 60 hPa and at a temperature of 100° C. for a period of 15 minutes, the mixture being distilled at the same time (distillate: 9.5 g of a water/allyl glycol mixture). 2.0 g of a solution of 1.0 g of p-toluenesulfonic acid, 0.4 g of water and 0.6 g of allyl glycol are then added and the mixture is stirred under a pressure of 90 hPa and at a temperature of 100° C. for a period of 3 to 4 hours until clear, the mixture being distilled at the same time (distillate: 14 g of a water/allyl glycol mixture). The clear mixture is now neutralized with 1.0 g of a 30% strength aqueous NaOH solution and then distilled again under a pressure of 1 hPa and at a temperature of 110° C. A vitreous product which is viscous at 100° C. and solid at room temperature is obtained. A virtually 100% yield and an average degree of glycosidation of 1.5 are determined by $^1$H-NMR.

43.4 g of the alkenyl glycoside I described above are heated to 80° C., 0.14 g of a solution of 1 g of H$_2$PtCl$_6$.6H$_2$O in 99 g of isopropanol (platinum content of the solution: 38 ppm) is added and 51.8 g of hydridopentamethyldisiloxane are added dropwise in the course of 15 minutes, during which the temperature rises to 100° C. The mixture is then stirred at 80° C. for a period of one hour and subsequently distilled under a pressure of 1 hPa and at 60° C. 60 g of a compound having the average formula

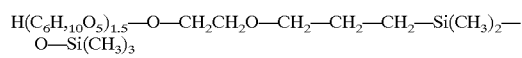

which is viscous and clear at 80° C. and solid at room temperature, are obtained.

EXAMPLE 2

56.0 g of the alkenyl glycoside I described in Example 1 under (A) are heated to 80° C., 0.33 g of a solution of 1 g of H$_2$PtCl$_6$.6H$_2$O in 99 g of isopropanol (platinum content of the solution: 38 ppm) is added and 166.6 g of a dimethyl/methylhydridopolysiloxane terminated by trimethylsilyl units and having 60 siloxy units and a content of Si-bonded hydrogen of 0.12% are added dropwise in the course of 45 minutes, during which the temperature rises to 100° C. The mixture is then stirred at 80° C. for a period of one hour and subsequently distilled under a pressure of 1 hPa and at 60° C. 215 g of a diorganopolysiloxane terminated by trimethylsilyl groups, which contains, as diorganosiloxy groups, units having the average formula

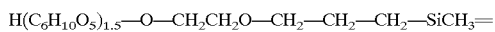

in addition to dimethylsiloxy groups, are obtained. The resulting organopolysiloxane is viscous at 80° C. and solid at room temperature.

EXAMPLE 3

(B) Preparation of a disiloxane containing hydroxyalkyl functional groups.

153 g of allyl glycol and 0.72 g of a solution of 1 g of $H_2PtCl_6.6H_2O$ in 99 g of isopropanol (platinum content of the solution: 38 ppm) are heated to 80° C., while stirring, and 329.6 g of hydridopentamethyldisiloxane are added dropwise over a period of 1 to 1.5 hours, during which the temperature rises to 110° C. The mixture is then stirred at 80° C. for a period of one hour and subsequently distilled under a pressure of 1 hPa and at 100° C. An almost colorless, clear oil having a viscosity of 9 mm²/s is obtained.

150 g of the disiloxane containing hydroxyalkyl functional groups described above are mixed with 39.6 g of glucose monohydrate and the mixture is stirred first under a pressure of 65 hPa and at a temperature of 60° C. for a period of one hour and then under a pressure of 65 hPa and at a temperature of 100° C. for a period of 15 minutes, the mixture being distilled at the same time (distillate: 2.5 g of water). 1.5 g of a solution of 0.75 g of p-toluenesulfonic acid, 0.3 g of water and 0.45 g of the disiloxane containing hydroxyalkyl functional groups described above are then added and the mixture is stirred under a pressure of 90 hPa and at a temperature of 100° C. for a period of 5 hours (distillate: 37 g of water). The mixture thus obtained is filtered. 57 g of a solid which contains a compound having the average formula

to the extent of 50% and pure polysaccharide to the extent of 50% are obtained.

What is claimed is:

1. A process for the preparation of an organosilicon compound containing glycoside radicals, which comprises, in a first stage
reacting, in the absence of an organic solvent, a monosaccharide and/or oligosaccharide (1) with a compound (2) of the formula $$HO-(R^2O)-R^4 \qquad (IV)$$

in which
$R^2$ is an alkylene radical, and
$R^4$ is an alkenyl radical,
in the presence of an acid, and in a second stage
neutralizing the acid and
reacting the glycoside-containing compound obtained in the first stage with an organosilicon compound (3) containing Si-bonded hydrogen, containing units of the formula

in which
$R^5$ are each independently an organic radical,
d is 0,1,2 or 3 and
e is 0,1,2 or 3, in the presence of a hydrosilation catalyst,
with the proviso that the sum of d+e is less than or equal to 3 and the organosilicon compound comprising units of the formula (V) contains at least one Si-bonded hydrogen atom per molecule.

* * * * *